United States Patent
Sasaki et al.

(10) Patent No.: US 6,656,119 B2
(45) Date of Patent: Dec. 2, 2003

(54) IMAGING DIAGNOSTIC APPARATUS AND MAINTENANCE METHOD OF THE SAME

(75) Inventors: Takuya Sasaki, Otawara (JP); Yasuo Miyajima, Utsunomiya (JP); Tsuyoshi Yoshie, Nasu-Gun (JP); Shinichi Hashimoto, Yaita (JP); Naohisa Kamiyama, Otawara (JP); Toshiaki Nakazato, Nasu-Gun (JP); Eiji Goto, Otawara (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/810,551

(22) Filed: Mar. 19, 2001

(65) Prior Publication Data

US 2003/0097054 A1 May 22, 2003

(30) Foreign Application Priority Data

Mar. 17, 2000 (JP) .................................. P. 2000-076808
Mar. 28, 2000 (JP) .................................. P. 2000-089707
Mar. 28, 2000 (JP) ...................................... 2000-89707

(51) Int. Cl.[7] .............................................. A61B 8/00
(52) U.S. Cl. ..................................................... 600/437
(58) Field of Search ............................... 600/437, 407, 600/409, 443, 447; 128/916; 382/128; 700/231, 237; 705/2–3, 52, 56

(56) References Cited

U.S. PATENT DOCUMENTS

| | | | | |
|---|---|---|---|---|
| 4,868,476 A | * | 9/1989 | Respaut | 318/632 |
| 5,321,520 A | * | 6/1994 | Inga et al. | 358/403 |
| 5,487,386 A | * | 1/1996 | Wakabayashi et al. | 600/437 |
| 5,603,323 A | * | 2/1997 | Pflugrath et al. | 600/437 |
| 6,012,458 A | * | 1/2000 | Mo et al. | 600/437 |
| 6,063,030 A | * | 5/2000 | Vara et al. | 600/437 |
| 6,101,407 A | * | 8/2000 | Groezinger | 600/407 |
| 6,178,225 B1 | * | 1/2001 | Zur et al. | 378/98.2 |
| 6,212,256 B1 | * | 4/2001 | Miesbauer et al. | 378/118 |
| 6,287,257 B1 | * | 9/2001 | Matichuk | 600/437 |
| 6,325,540 B1 | * | 12/2001 | Lounsberry et al. | 378/207 |
| 6,356,780 B1 | * | 3/2002 | Licato et al. | 600/407 |

* cited by examiner

Primary Examiner—Francis J. Jaworski
(74) Attorney, Agent, or Firm—Oblon, Spivak, McClelland, Maier & Neustadt, P.C.

(57) ABSTRACT

A medical imaging diagnostic apparatus is maintained by means of a remote computer connected to a communication line. This maintenance includes: generating log data concerning a use state of a medical imaging diagnostic apparatus; transmitting the thus generated log data to the remote computer via the communication line; storing the thus transmitted log data as data that configures a database on the remote computer; and analyzing the use state of the medical imaging diagnostic apparatus so that the use state can be displayed based on the stored log data.

17 Claims, 10 Drawing Sheets

| PATIENT INFORMATION INPUT | 2001/2/14 | 10:20:15 |
| B-MODE SCANNING START | 2001/2/14 | 10:30:25 |
| FREEZE ON | 2001/2/14 | 10:33:35 |
| FREEZE OFF | 2001/2/14 | 10:33:55 |
| FREEZE ON | 2001/2/14 | 10:34:15 |
| STILL IMAGE RECORDING | 2001/2/14 | 10:34:30 |
| ⋮ | ⋮ | ⋮ |
| DOPPLER START | 2001/2/14 | 10:40:15 |
| FREEZE ON | 2001/2/14 | 10:42:20 |
| STILL IMAGE RECORDING | 2001/2/14 | 10:42:45 |
| VTR START | 2001/2/14 | 10:44:35 |
| VTR END | 2001/2/14 | 10:45:35 |
| ⋮ | ⋮ | ⋮ |
| PATEINT INFORMATION INPUT | 2001/2/14 | 11:05:15 |
| ⋮ | ⋮ | ⋮ |

| TECHNICIAN ID | DEVICE ID | PATIENT ID | EXAMINATION DATE AND TIME | B-MODE USE TIME | DOPPLER MODE USE TIME | COLOR MODE USE TIME | M-MODE USE TIME | FREEZE COUNT | STILL IMAGE RECORDING COUNT | VTR RECORDING COUNT |
|---|---|---|---|---|---|---|---|---|---|---|
| OP1 | A1 | PT1 | XX/XX/XX | XX:XX:XX | XX:XX:XX | XX:XX:XX | XX:XX:XX | F1 | R1 | V1 |
| OP2 | A2 | PT2 | XX/XX/XX | XX:XX:XX | XX:XX:XX | XX:XX:XX | XX:XX:XX | F2 | R2 | V2 |
| OP3 | A3 | PT3 | XX/XX/XX | XX:XX:XX | XX:XX:XX | XX:XX:XX | XX:XX:XX | F3 | R3 | V3 |
| ... | ... | ... | ... | ... | ... | ... | ... | ... | ... | ... |
| OPn | An | PTn | XX/XX/XX | XX:XX:XX | XX:XX:XX | XX:XX:XX | XX:XX:XX | Fn | Rn | Vn |

FIG.5

IMAGING DIAGNOSTIC APPARATUS AND MAINTENANCE METHOD OF THE SAME

BACKGROUND OF THE INVENTION

1. Field of the Invention

The present invention relates to a medical imaging diagnostic apparatus such as ultrasonic diagnostic apparatus and a maintenance method of the same, and more particularly to a technique suitable to remote maintenance from a remote computer connected to a medical imaging diagnostic apparatus via a communication line.

2. Description of Related Art

Conventionally, it has been well known that an ultrasonic diagnostic apparatus is equipped with a general function concerning ultrasonic image diagnosis which is an object of such apparatus and a service/maintenance function for changing system settings, performing system diagnosis, and changing (upgrading or the like) computer software such as control programs incorporated in the apparatus to its latest version.

Such service/maintenance function is generally incorporated in a main frame of an ultrasonic diagnostic apparatus. Thus, the service/maintenance work is generally performed by operators such as service personnel directly operating the main frame of the ultrasonic diagnostic apparatus. In this case, it has been required for service personnel to visit hospital or the like in which the apparatus is installed when service/maintenance work is performed by using the ultrasonic diagnostic apparatus equipped with the service/maintenance function. Therefor, a work time required for service/maintenance work is completed by service personnel is increased by a time required for movement to facility. This time corresponds to a down time caused by a fault of an ultrasonic diagnostic apparatus from the viewpoint of an operator who operates the ultrasonic diagnostic apparatus. Thus, as this time is increased, a time in which the ultrasonic diagnostic apparatus cannot be used is increased as in the case of a fault. That is, there is a high possibility that an increased time of service/maintenance work causes a problem with medical activities such as medical diagnosis using the ultrasonic diagnostic apparatus.

In the case where the computer software incorporated in the apparatus is changed in the service/maintenance work for the ultrasonic diagnostic apparatus, it is required to do a work of distributing or managing a recording medium having such change recorded therein. However, the distribution or management of such recording medium is generally complicate and cumbersome, and is time consuming, thus causing incorrect operation of service personnel.

Further, there has been a problem that acquisition or management of information concerning contents of service/maintenance work for the ultrasonic diagnostic apparatus is generally complicate and cumbersome, and is time consuming as well.

Furthermore, in view of an aspect of maintenance of the ultrasonic diagnostic apparatus, data concerning the use state of each apparatus or maintenance is recorded and stored, and the data is referred to or analyzed whenever or wherever necessary, thereby making it possible to significantly improve efficiency of the service/maintenance work. In particular, if the data on the use state of each apparatus can be analyzed in association with operator or patient data, such analysis is expected to be very useful in hospital management as well as in efficient maintenance work.

However, it is currently difficult to perform service maintenance capable of analyzing the use state of such each apparatus.

In recent years, other medical imaging diagnostic apparatuses as well as the above ultrasonic diagnostic apparatus are equipped with computer network related functions with the advancement of linkage with general-purpose computer technology.

As such computer network related functions, there are known: for example, a function for enabling remote service from a remote computer connected via a communication line; a function for providing access patient data on a database of a local network; or a function concerning remote diagnosis. Using these functions enables for example service works such as fault diagnosis, maintenance, and software version management for a medical imaging diagnostic apparatus from a remote computer, or remote diagnosis by remote doctors, or intensive management of patient image data. In this manner, it is expected that efficiency of image diagnosis which is an object of a medical imaging diagnostic apparatus is improved more remarkably.

However, in a medical imaging diagnostic apparatus, apart from convenience obtained by such computer network related functions, the following problems arise. That is, in this medical imaging diagnostic apparatus, a concept of security management is not adopted because the operator's privilege is limited. In other words, this diagnostic apparatus does not consider, in particular, a so called concept of "login" for recognizing the operator during apparatus startup. Thus, if such medical imaging diagnostic apparatus is equipped with computer network related functions, maloperation or malfunction caused by the operator's unintentional data change or the like or activities of interpolation caused by an malicious third person is likely to occur. In this manner, there is a concern for security problems such as occurrence of apparatus maloperation or malfunction or finding weak points of patient information security.

For example, in the above medical imaging diagnostic apparatus, there is a possibility that an apparatus environment setting file is erased or rewritten by the operator's incorrect operation; the apparatus cannot be restarted; or apparatus maloperation which is hardly judged to be abnormal clearly. In addition, in this medical imaging diagnostic apparatus, there is apprehension that diagnosis image data on patients in intensive care, patient name or private patient data, electrical medical chart information on patients are used in an malicious manner; a third person who spoofs an examination personnel, an apparatus service personnel, or a doctor makes illegal copy (steal), interpolation, and erasing.

In order to overcome the above described security problems, it is required to construct and manage a system for restricting privilege relevant to functions requiring security, and preventing spoofing for such privileged persons. However, such security management requires special knowledge. Thus, it is considered that educating and training detailed operation for all operators lose convenience of a medical imaging diagnostic apparatus, lowers efficiency of diagnostic activities on which doctors should be concentrated, or patient service is lowered. Because of this, it is expected that there occur problems such as an increased diagnostic cost or an increased cost of a medical system.

In the recent medical imaging diagnostic apparatus, available functions are prone to be diversified and complicated. Thus, a function for customizing operating environment for each operator is indispensable so that frequently used functions can be easily used. In addition to this, as described above, in recent years, a medical imaging diagnostic apparatus is connected to a network, image information or patient information and any other information required for diagnosis or apparatus setup are often acquired or provided via this network. Furthermore, there are increased opportunities that general operator who is not familiar with setup unlike service personnel performs high-level apparatus setup because of enhancement of peripheral devices and other reason.

However, in the case where a general operator operates all of the above described functions, the following problems occur. For example, operation under the operating environment set by another operator can be easily performed, and thus, such environment can be easily changed by an operator other than an operator using such operating environment. In addition, the use privilege given to an operator relevant to functions is insufficient merely by providing two levels for service personnel or general operators. For example, it is currently difficult to set an administrator level and a user level relevant to a general operator. Therefore, in the worst case, it is expected that a serious failure which causes a problem with apparatus startup will occur.

SUMMARY OF THE INVENTION

The present invention has been made in view of the foregoing circumstances. It is a first object of the present invention to reduce a time required for service/maintenance and a down time of a medical imaging diagnostic apparatus such as ultrasonic diagnostic apparatus.

It is a second object of the present invention to limit a privilege relevant to specific functions such as remote diagnosis of a medical imaging diagnostic apparatus such as ultrasonic diagnostic apparatus, patient data management or remote service function, and preventing spoofing, thereby eliminating a possibility that apparatus malfunction occurs or an apprehension that patient privacy is infringed, and to enhance convenience of such specific functions more remarkably.

It is a third object of the present invention to restrict a privilege by person or organization relevant to specific functions such as ultrasonic diagnostic apparatus or specific functions such as patient data management or remote service function and identify a person or organization registered in advance to an operator or a person connected from a remote site, thereby making it possible to easily set these restrictions without any special knowledge, safely utilize the convenience caused by network functions or the like, and provide highly satisfied medical activities to a patient while reducing medical cost.

It is a fourth object of the present invention to record and store data concerning the use state of each apparatus or maintenance in maintenance of a medical imaging diagnostic apparatus such as ultrasonic diagnostic apparatus as required so that the data can be analyzed.

In order to achieve the above objects, a medical imaging diagnostic apparatus and maintenance method of the same according to the present invention has the following aspects.

According to a first aspect of the present invention, a medical imaging diagnostic apparatus such as ultrasonic diagnostic apparatus and a service system (a maintenance system) are connected with each other via a network to make communication, whereby required data is transmitted and received, and service/maintenance work is achieved under remote control. This makes it possible to achieve the foregoing object, and significantly reduce a time required for service/maintenance and a down time of a medical imaging diagnostic apparatus. In addition, there is provided an effect that a release time during software upgrading can be reduced, and the corresponding error does not occur.

According to a second aspect of the present invention, in addition to the above configuration, a database is provided over a network, thereby maintaining and managing information such as software upgrade data, system diagnosis data, and service/maintenance work update history data. In this manner, information on the service/maintenance work scope can be integrally managed.

The information obtained by system diagnosis can include: operation state of each internal unit of an ultrasonic diagnostic apparatus (for example, unit A: Diagnosis result, Normal, unit B: Error, and unit C: Error with block C in the unit); probe characteristics (for example, lowered 56-th element sensitivity of a total of 192 elements, 60 [dB] or more, entire element sensitivity, or −2 [dB] or more as compared with a probe just purchased); a use time of application used in the ultrasonic diagnostic apparatus (for example, application A, use time, 5 hours, and application B, 2 hours or the like). Based on these items of information, there can be provided service for preventing the apparatus from being degraded in characteristics, and maintaining its performance.

For example, faults/abnormalities are sensed earlier by units, part and unit replacement or the like is performed, whereby its performance can be maintained, making it possible to take velocity judgment or response to the operation state of each apparatus. In addition, if a failure is not so serious that the apparatus is not activated immediately, it is possible to display a warning message on the apparatus for an operator, to dispatch service personnel immediately, to notify a faulty unit in advance to service personnel, and to notify service personnel so as to make replacement on the spot if required. In addition, the degraded performance of an ultrasonic probe causes the degraded performance of the entire ultrasonic diagnostic apparatus. Since such ultrasonic probe is disposable, proper replacement is made by grasping the degree of characteristic degradation, making it possible to maintain its performance. For example, in the case where a faulty element in the ultrasonic probe is found, it is regarded as a fault. In this case, the user can arrange service personnel to replace such faulty element with a replacement element. In the case where the entire characteristics are degraded, such probe can be replaced. In addition, it is possible to recycle a used item as required.

According to a third aspect of the present invention, there is provided functions required for repair, fault diagnosis, periodic inspection or the like, for example, control of apparatus operation which is different from general diagnosis, storing the internal state of the apparatus, or acquisition of information or data obtained. This apparatus is restricted to only account having its privilege in which access permission of programs and data required for initiating these functions is different from an account for logging in the apparatus in a general examination state; and an account having the administrator's privilege.

According to a fourth aspect of the present invention, there is provided an apparatus connected to a network with wire or wirelessly. This apparatus has functions or the like used for any other purpose than diagnosis such as repair, fault diagnosis, periodic inspection, for example, functions for providing access via a network connected with wire or wirelessly, thereby controlling an operation of the apparatus, storing into the apparatus the internal state of the apparatus, and acquiring information/data obtained. This apparatus comprises means for automatically setting access privileges of these functions in accordance with predetermined procedures. The means can include startup switch means, pointer means, voice startup selection means or the like.

According to the fourth aspect, there can be provided a configuration in which, of the functions of the apparatus relevant to an account capable of accessing the foregoing functions, the individual settings of startup enable or disable are provided in the apparatus or over only a network to which the apparatus belongs with respect to a function for providing access to the hospital internal information or patient information in the apparatus and in a network to which the apparatus belongs.

According to a fifth aspect of the present invention, there is provided an ultrasonic diagnostic apparatus connected to a network, comprising functions for providing access any other purpose than diagnosis such as apparatus repair, fault diagnosis, or periodic inspection; controlling an operation of the apparatus, and/or storing the internal state or the like of the apparatus in the apparatus, and/or acquiring information/data obtained, a pointer for automatically enabling/disabling these functions in accordance with predetermined procedures; or a switch containing startup selection by voice.

According to the above fourth and fifth aspects, one of the following configurations is possible.

1) It is possible to provide means for automatically changing an account password for making connection to a network to which the apparatus belongs during apparatus startup. In this case, a password after changed is transmitted as a message containing E-mail over the same or different network specified in advance. This transmission can be performed in a file that exists on the apparatus.

2) It is possible to provide means for detecting and recording access caused by an illegal password or account. In this case, it is desirable to record an access destination.

3) A password can be encoded.

4) Data on password can be transmitted divided in plurality. In this case, if illegal access reaches a predetermined count, a function is stopped, and such count can be transmitted as a message containing the corresponding file or mail over the same or different network or over the apparatus.

5) A password in accordance with a security card system can be used. This system is intended to issue one or plural characters and/or numerals changed in a predetermined logic with an elapse of time and to issue the same to the apparatus side in the same logic.

6) User recognition means using electrical authentication can be provided.

7) User recognition means for supervising an IP address of TCP/IP can be provided.

8) User recognition means for supervising physiological characteristics of individuals registered in advance can be provided. In this case, the physiological characteristics include fingerprint, iris pattern, voiceprint, and facial characteristics, for example.

9) In the case where operation is not performed for a predetermined period of time, it is possible to provide means for automatically invalidating an access privilege or release a initiated function.

According to a sixth aspect of the present invention, there is provided an apparatus for automatically performing password authentication or electrical authentication which changes with an elapse of time in order to correctly recognize the apparatus when the apparatus voluntarily communicates with a service center or the like for the purpose of a service function.

According to a seventh aspect of the present invention, operator specific login is performed by using at least one of an operator code and password, and operation in the operator specific setting environment caused by the operator logged in is permitted.

According to an eighth aspect of the present invention, operator registration is performed, two or more levels are determined by the operator, and available functions are limited according to such level.

The present invention is based on each of the above described aspects, and is constructed in the following mode.

A maintenance method of a medical imaging diagnostic apparatus according to the present invention is directed to a method of maintaining a medical imaging diagnostic apparatus by a remote computer connected via a communication line, the method comprising the steps of: generating log data concerning a use state of the medical imaging diagnostic apparatus; transmitting the generated log data to the remote computer via the communication line; storing the transmitted log data as data configuring a predetermined database on the remote computer; and analyzing the use state of the medical imaging diagnostic apparatus so that the use state can be displayed based on log data stored as data configuring the database.

In the present invention, the medical imaging diagnostic apparatus is directed to an ultrasonic diagnostic apparatus having an ultrasonic probe, wherein the analysis result of the use state of the medical imaging diagnostic apparatus can include at least one of the number of patients diagnosed within a predetermined period of time by the ultrasonic diagnostic apparatus, each use time of ultrasonic diagnostic Doppler mode, B mode, M mode, CFM (Color Flow Mapping) mode, Angiographic mode, TDI (Tissue Doppler Imaging) mode, THI (Tissue Harmonic Imaging) mode, and measurement mode used by the ultrasonic diagnostic apparatus, ultrasonic image freeze count displayed by the ultrasonic diagnostic apparatus, the ultrasonic image recording count, and a rate of the recording count to the freeze count.

In the present invention, the medical imaging diagnostic apparatus is directed to an ultrasonic diagnostic apparatus having an ultrasonic probe, wherein data configuring the database is at least one of degradation information on the ultrasonic probe; information on date and time when a measurement value obtained by an acceleration sensor provided at the ultrasonic probe exceeds a predetermined value and information on the count when the measurement value obtained by the acceleration sensor exceeds a predetermined value.

In the present invention, the medical imaging diagnostic apparatus is directed to an ultrasonic diagnostic apparatus having an ultrasonic probe, wherein the ultrasonic diagnostic apparatus can comprise: a probe holder for holding the ultrasonic probe; a phantom consisting of a standard test body for phantom testing equipped in the probe holder; mean for obtaining an ultrasonic image of the phantom by the ultrasonic probe held in the probe holder; and means for transmitting the ultrasonic image of the phantom being data for obtaining degradation information on the ultrasonic probe to the remote computer.

A maintenance method of a medical imaging diagnostic apparatus according to the present invention comprises the steps of: generating log data concerning a use state of a medical imaging diagnostic apparatus; recording the thus generated log data on a predetermined recording medium; and analyzing the use state of the medical imaging diagnostic apparatus so that the use state can be displayed based on the log data on the recording medium.

A medical imaging diagnostic apparatus according to the present invention comprises: log generating means for generating log data concerning a use state of a medical imaging diagnostic apparatus; log recording means for recording the log data generated by the log generating means on a predetermined medium; and analysis means for analyzing the use state of the medical imaging diagnostic apparatus so that the use state can be displayed based on the log data recorded on the recording medium by the log recording means.

A medical imaging diagnostic apparatus according to the present invention comprises: input means configured so as to enable maintenance by means of a remote computer connected via a communication line, the input means being provided at the medical imaging diagnostic apparatus, the input means being adopted to input information concerning a system user; operating means provided at the medical imaging diagnostic apparatus, operating means being adopted to instruct change to a predetermined system maintenance mode; transmission means for, when a change to the system maintenance mode is instructed by the operating means, transmitting information concerning the system user inputted by the input means and date and time information to the remote computer; and means for switching a current state into a state for enabling at least one of system diagnosis of the medical imaging diagnostic apparatus, system setting change thereof, and control program change based on a signal transmitted from the remote computer via the communication line in response to the information transmitted by the transmission means.

A maintenance method of a medical imaging diagnostic apparatus according to the present invention is directed to a method of maintaining a medical imaging diagnostic apparatus by means of a remote computer connected via a communication line, the method comprising the steps of: inputting information concerning a system user to the medical imaging diagnostic apparatus; instructing switching into a system maintenance mode for enabling at least one of system diagnosis of the medical imaging diagnostic apparatus, system setting change, and control program change based on a signal transmitted from the remote computer by operating the medical imaging diagnostic apparatus; when switching into the system maintenance mode is instructed, transmitting to the remote computer via the communication line, information concerning the system user and date and time information; and storing the thus transmitted information concerning the system user and date and time information on a predetermined recording medium on the remote computer.

Additional objects and advantages of the invention will be set forth in the description which follows, and in part will be obvious from the description, or may be learned by practice of the invention. The objects and advantages of the invention may be realized and obtained by means of the instrumentality and combinations particularly pointed out hereinafter.

BRIEF DESCRIPTION OF THE DRAWINGS

The other configuration and advantageous effect according to the present invention becomes apparent from a description taken in conjunction with the following embodiments of the invention and the accompanying drawings in which:

FIG. 5 is a view illustrating an analysis example of the use state of the ultrasonic diagnostic apparatus;

FIG. 9A is a partial cross section viewed from a front view, and FIG. 9B is a partial cross section viewed from a side face.

DETAILED DESCRIPTION OF THE PREFERRED INVENTION

Hereinafter, preferred embodiments of a medical imaging diagnostic apparatus and a maintenance method of the same according to the present invention will be described with reference to the accompanying drawings.

First Embodiment

Figure 1:
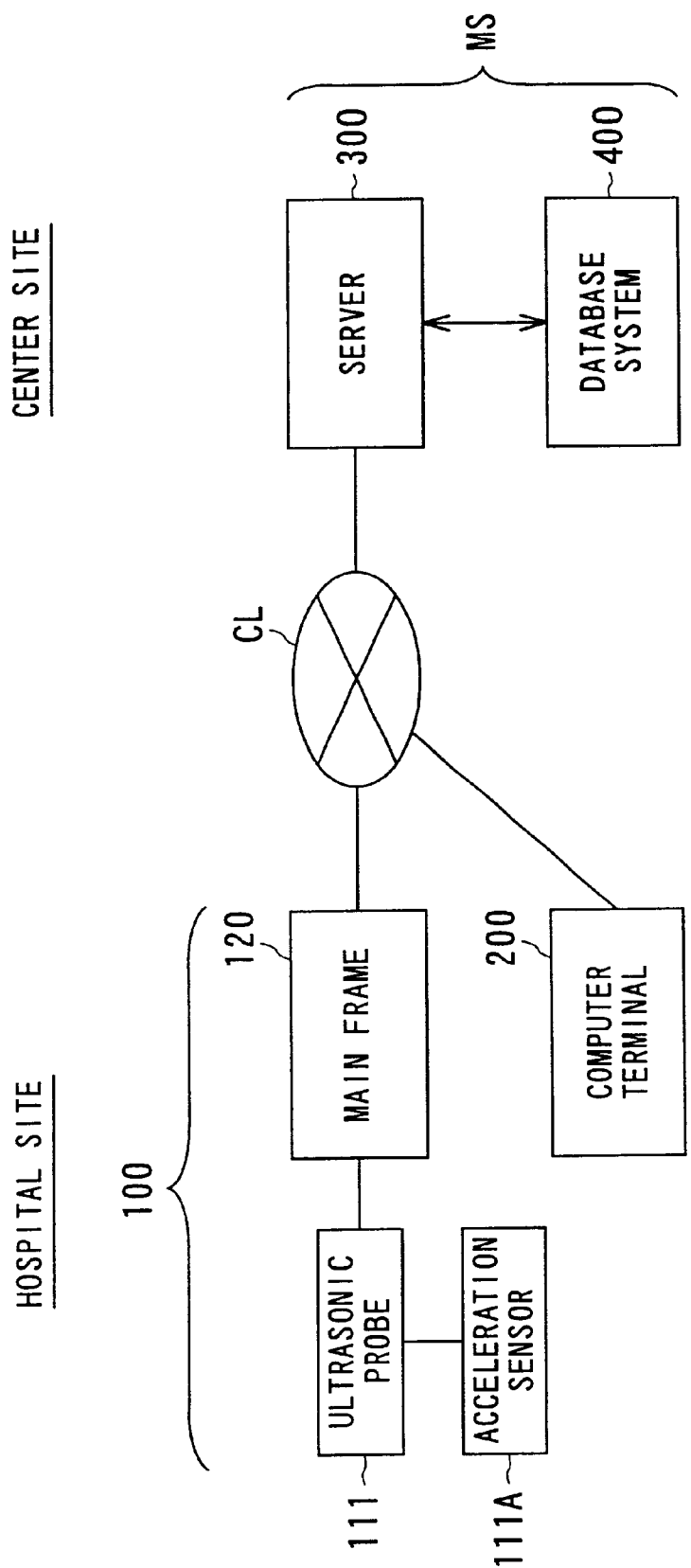
FIG. 1 is a schematic block diagram illustrating a medical imaging diagnostic apparatus and a maintenance method of the same according to a first embodiment of the present invention.

FIG. 1 illustrates an outline of a maintenance system of a medical imaging diagnostic apparatus according to a first embodiment of the present invention (ultrasonic diagnostic apparatus in the present embodiment). In FIG. 1, an ultrasonic diagnostic apparatus 100 shown as an example of medical imaging diagnostic apparatuses and a computer terminal 200 such as PC (personal computer) used by a system user are installed at a hospital site at which image diagnosis of a patient is performed.

In FIG. 1, a maintenance system MS configuring a service system is disposed at a remote center at which maintenance of the ultrasonic diagnostic apparatus 100 should be controlled. These maintenance system MS, ultrasonic diagnostic apparatus 100, and computer terminal 200 enable communication of various control signals or information concerning maintenance of the ultrasonic diagnostic apparatus 100 based on standardized communication protocols such as TCR/IP via a communication line CL such as a public line or a leased line, as shown in FIG. 1.

Now, the ultrasonic diagnostic apparatus 100 installed at the hospital site and the maintenance system MS installed at the center site will be described separately in detail.

First, the ultrasonic diagnostic apparatus 100 installed at the hospital site applies a general system for transmitting and receiving ultrasonic beams to and from a diagnosis site in a patient, thereby acquiring/displaying an ultrasonic image based on the ultrasonic echo signal. This apparatus is composed of an ultrasonic probe 111 and a main frame 112 to which this ultrasonic probe 111 is connected.

The ultrasonic probe 111 is applied as various types of sector electronic scanning type, linear scanning type, and mechanical scanning type or the like. This probe has a probe tip end at which a plurality of piezoelectric transducers are arranged in a array shape. According this ultrasonic probe 111, a driving voltage from the main frame 112 is converted into an ultrasonic pulse signal, and the ultrasonic pulse signal is transmitted from the probe tip end in a desired direction of a diagnosis site in a patient. In addition, at the probe tip end, the ultrasonic echo signal reflected at a boundary at which acoustic impedance of the internal tissues of a patient is different from another or scattered backwardly by a fine scattering body, is converted into the corresponding voltage signal, and the voltage signal is supplied to the mainframe 112.

In addition, this ultrasonic probe 111 has an acceleration sensor 111a provided at a proper position of its main frame (not shown). This acceleration sensor 111a measures acceleration caused by vibration or the like of the ultrasonic probe 111, and supplies the measurement value to the main frame 112.

Figure 2:
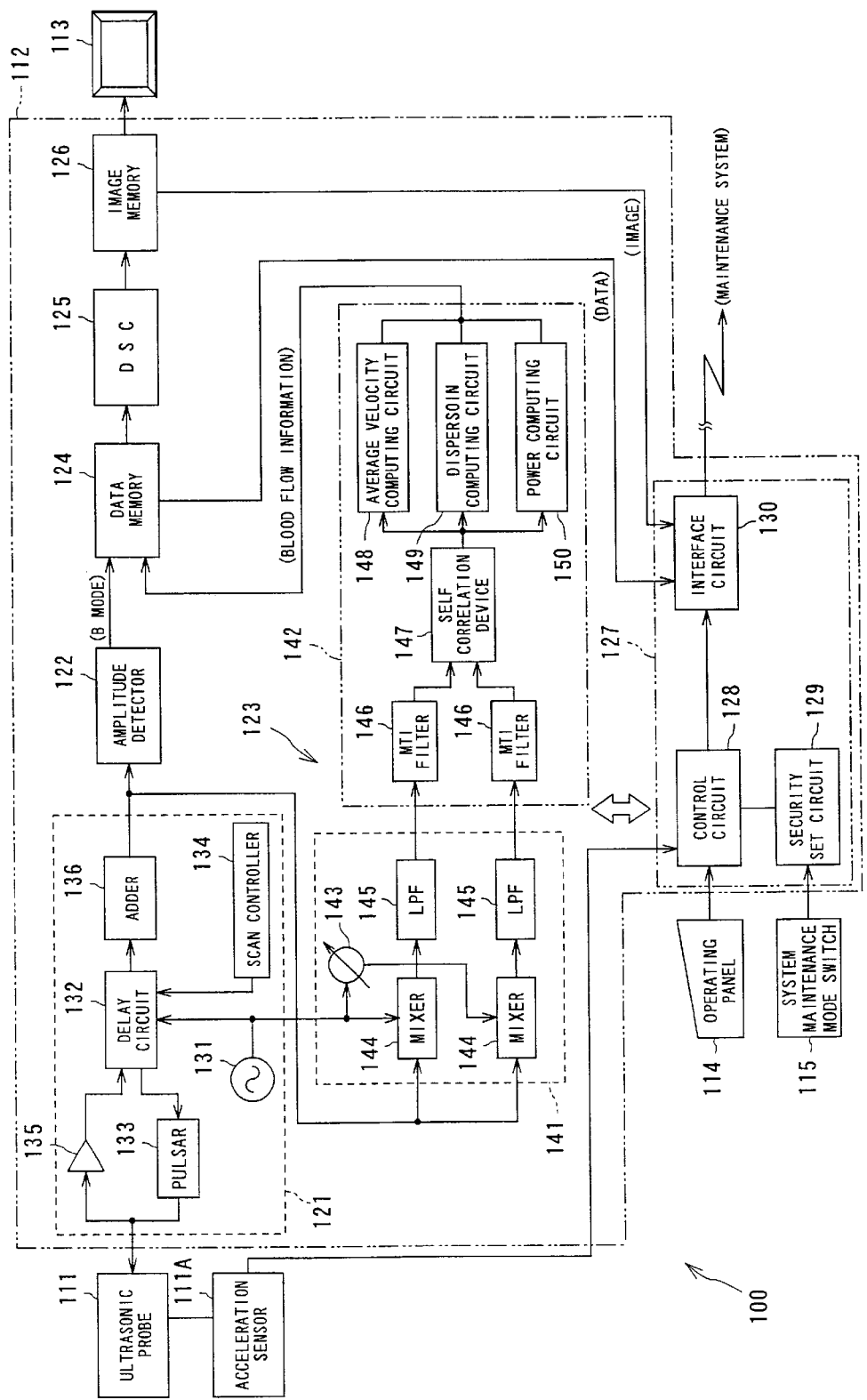
FIG. 2 is a schematic block diagram depicting an entire configuration of an ultrasonic diagnostic apparatus according to the first embodiment.

FIG. 2 illustrates an outline of a main frame 112 of an ultrasonic diagnostic apparatus 100. In FIG. 2, a monitor 113, an operating panel 114, and a system maintenance mode switch 115 are mounted on the main frame 112.

Among them, the operating panel 114 is equipped with input devices such as various modes used in ultrasonic diagnosis of a patient (for example, B mode, Doppler mode, M mode, CFM mode, angiographic mode, TDI mode, THI mode, or measurement mode and the like), an ultrasonic image freeze button, a still image/VTR recording button, and a button, a switch, a keyboard, a mouse, and a trackball for inputting an instruction from a user such as any other condition setting or change.

In addition, the system maintenance mode switch 115 is used during maintenance of the ultrasonic diagnostic apparatus 100. For example, this switch is integrally mounted as an input device on the operating panel 114 or is composed of instructing means caused by software such as pointer, menu, and bottom displayed on a screen of the monitor 113. This system maintenance mode switch 115 can be employed as other instructing means for voice startup/selection and the like without being limited thereto.

On the above main frame 112, as shown in FIG. 2, there are mounted: a transmitter/receiver circuit 121 connected to the ultrasonic probe 111; an amplitude detector 122 placed at the receiver side of this transmitter/receiver circuit 121; a blood flow information detector 123; a data memory 124; a DSC (digital scan converter) 125; an image memory 126; and a control portion 127 serving as a nucleus for controlling the entirety of these modalities.

The transmitter/receiver circuit 121 comprises: an oscillator (pulse generator) 131; a transmitting and receiving delay circuit 132; a pulsar 133; a scan controller 134; a pre-amplifier 135; and an adder 136, as shown in FIG. 2.

The oscillator 131 generates a rate pulse that determines a repetition frequency of ultrasonic beams from the ultrasonic probe 111; divides the rate pulse into the number of transmission channels according to the number of vibrators of the ultrasonic probe 111; and transmits the divided pulses to a delay circuit 132. The delay circuit 132 variably set a delay time according to a timing signal instructed from the scan controller 134; adds the delay time to a rate pulse; and supplies the added pulse to the pulsar 133 for each transmission channels. The pulsar 133 supplies a voltage pulse by each vibrator (transmission channel) of the ultrasonic probe 111 at a timing at which the rate pulse has been received.

In this manner, in the transmitter/receiver circuit 121, a timing of the voltage pulse supplied to each vibrator of the ultrasonic probe 111 is changed, whereby the ultrasonic beams emitted into a patient from the ultrasonic probe 11 are electronically scanned or focusing is applied. At this time, a delay time supplied to the delay circuit 132 under the control of the scan controller 134 is varied, whereby the direction (raster direction) of ultrasonic beams can be varied.

The thus transmitted ultrasonic beams are reflected on a discontinuous face of the acoustic impedance in a patient. This reflection ultrasonic signal is received by the ultrasonic probe 111 again, and is converted into a reflection wave signal of the corresponding voltage quantity. This reflection wave signal is amplified by means of a pre-amplifier 135, and the same delay time as during transmission is assigned by means of the delay circuit 132. Then, the signal is added by means of the adder 136, and is transmitted to the amplitude detector 122 and the blood flow information detector 123.

The amplitude detector 122 detects the intensity of a reflection wave in each of the raster directions of ultrasonic beams upon receipt of an output from the adder 136 in the transmitter/receiver circuit 121. Then, this detector transmits the detected signal that is luminance information on each raster, that is, B-mode image (tomographic image) information to a DSC 125 via a data memory 124.

The blood flow information detector 123 comprises a Doppler shift detector 141 and a color Doppler MTI (Moving Target Indicator) computing portion 142.

The Doppler shift detector 141 is a circuit that detects a Doppler deviation frequency in accordance with a quadrature wave detection system. This detector comprises a phase shifter 14 for converting a phase by 90 degrees into an output side of the oscillator 131 in the transmitter/receiver circuit 121, for example, mixers 144,144 divided into two channels at the output side of the adder 136; and low pass filters (LPF) 145 and 145.

The mixers 144 and 144 each multiplies an output of the adder 136, an output of the oscillator 131, and an output of the phase shifter 143, respectively, thereby obtaining a Doppler deviation frequency and a high frequency component (doubled transmission frequency +Doppler deviation frequency), and transmits them to each of the LPFs 145 and 145.

The LPFs 145 and 145 each eliminate a high frequency component from an output of each of the mixers 143 and 143, and transmits to the MTI computing portion 142 a cosin component and a sine component capable of detecting the polarty of a Doppler deviation frequency.

The MTI computing portion 142 comprises an A/D converter (not shown), MTI filters 146 and 146, a self correlation device 147, an average velocity computing circuit 148, a dispersion computing circuit (velocity distribution computing circuit) 149, and a power computing circuit 150 in order at the output side of each of the LPFs 145 and 145.

The MTI filters 146 and 146 each consist of a digital filter having its high pass characteristics, for example. These filters each eliminates an undesired refection wave (clutter component) from a stationary reflection body (blood vessel wall or cerebral wall) in response to an output after each LPF has been A/D converted, and supplies an average velocity, dispersion (velocity distribution), and power to the corresponding computing circuits 148 to 150 via a self correlation device 147.

Each of the average velocity, deviation, and power computing circuits 148 to 150 computes an average velocity (or maximum velocity), velocity distribution (or velocity distribution value), and scattering power information from a blood flow, and supplies them as blood flow information to the DSC 125 via the data memory 124.

The DSC 125 converts B-mode image information from the amplitude detector 122 and blood flow information from the blood flow detector 123 into an image format in accordance with a standard television system, and outputs these images to a monitor 113 via an image memory 126. In this manner, in a normal examination state, a B-mode image or blood flow information in accordance with a predetermined format is displayed on a screen of the monitor 113.

The control portion 127 contains: a control circuit 128 connected to the operating panel 14; a security setting circuit 129 connected to the system maintenance mode switch 115; and a communication interface circuit 130.

The control circuit 128 incorporates a microcomputer that contains a recording medium such as CPU and memory, for example. A processing algorithm recorded in the recording medium in advance is executed by a CPU, whereby the operation or function of each constituent element in the ultrasonic diagnostic apparatus 100 is controlled based on the user's instruction from the operating panel 114 or system maintenance mode switch 115, and processing concerning preset maintenance preset by controlling communication with the maintenance system MS at the center site is controlled, is executed during maintenance such as repair, fault diagnosis, periodic maintenance of the ultrasonic diagnostic apparatus 1.

In particular, this control circuit 128 generates/acquires log data that is data on the use state of the ultrasonic diagnostic apparatus 00 by means of the CPU processing; stores the log data in a storage medium such as memory or the like in the control circuit 128, for example, and periodically transmits the log data to the maintenance system MS through a communication line CL via the interface circuit 130.

The security setting circuit 129 incorporates a microcomputer having a CPU and a recording medium or the like, for example. The CPU executes a processing algorithm recorded as software or firmware in advance in such recording medium, whereby a logon (login) screen prompting user ID or password entry is displayed on a monitor 113, for example, when the apparatus 100 is powered ON; only a switch required for such input operation (a switch on operating panel 114 or system maintenance mode switch 115) is enabled, and operation of the other switch or function and the like is restricted according to the user.

In this case, it is possible to restrict a privilege for operating a service function or a patient information access function for a user who undergoes logon by an account such as default user preset immediately after the power has been supplied. The security setting circuit 129 can be configured integrally with the control circuit 128.

The maintenance system MS placed at the center site comprises: a server 300 that functions as a remote computer connected to the ultrasonic diagnostic apparatus 100 via a communication line CL; and a database system 400 for managing data on the use state of the ultrasonic diagnostic apparatus 100 to be processed/analyzed by this server 300, as shown in FIG. 1 described previously.

Figures 3, 4:
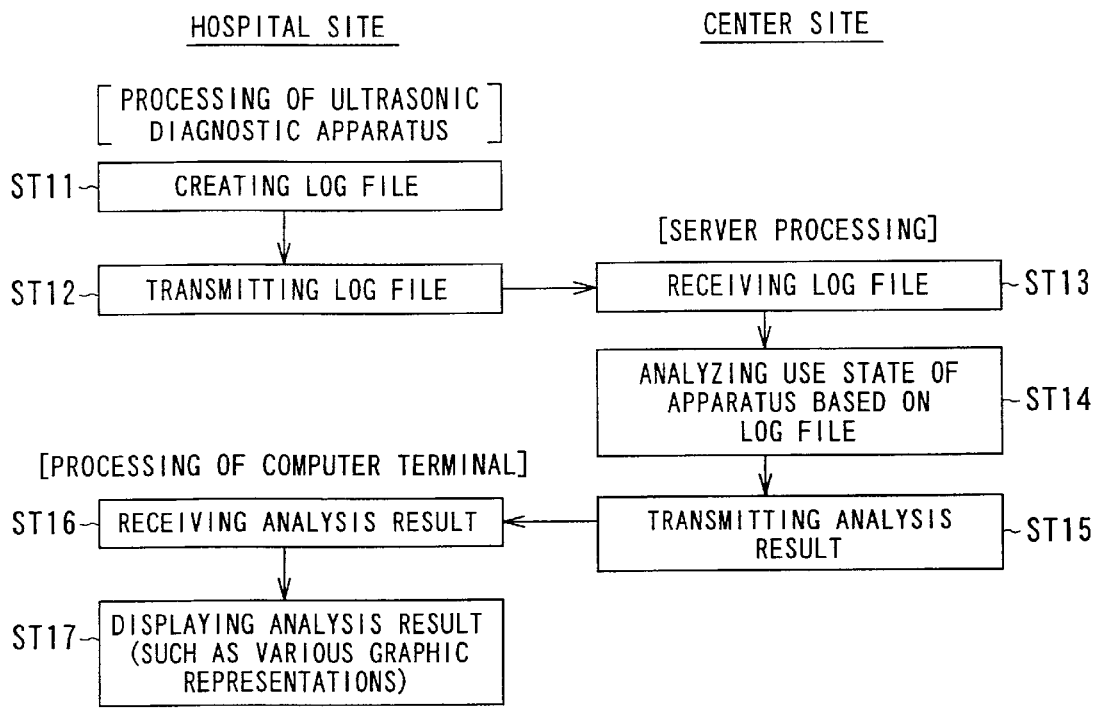
FIG. 3 is a chart illustrating a processing sequence between the ultrasonic diagnostic apparatus and maintenance system.
FIG. 4 is a view illustrating an example of log data used in analyzing a use state of the ultrasonic diagnostic apparatus.

FIG. 3 illustrates an outline of a processing sequence between the ultrasonic diagnostic apparatus 100 at the hospital site and the maintenance system MS at the center site.

In FIG. 3, the ultrasonic diagnostic apparatus 100 generates log data (a log file or an update history file) as data on the use state of the ultrasonic diagnostic apparatus 100 through processing of the control portion 127 (step St11).

FIG. 4 shows an example of the log data. The log data in the present embodiment, as shown in FIG. 4, records in time series date and time information on the contents of operations of the ultrasonic diagnostic apparatus by a system user such as technician (for example, new patient information input, B-mode scanning start, freeze ON, freeze OFF, freeze ON, still image recording, . . . , Doppler mode start, freeze ON, still image recording, VTR recording, VTR ending, . . . , next patient information input, . . . , or the like), Next, in FIG. 3 described previously, the ultrasonic diagnostic apparatus 100 transmits the thus generated log data periodically, for example, every one month to the maintenance system MS at the center via a communication line CL (step St12).

In response to this, as shown in FIG. 3, when the maintenance system MS receives log data transmitted from the ultrasonic diagnostic apparatus 100 through processing of the server 300 (step St13), such log data is stored as data that configures a database on the database system 400, and the use state of the ultrasonic diagnostic apparatus 100 is analyzed based on such log data (step St14).

FIG. 5 shows an example of the analysis result data obtained by this server 300. The analysis result data shown in FIG. 5 contains information for each item such as technician ID (OP1, OP2, OP3, . . . , OPn) that corresponds to identification number of each technician that is a system user; device ID (A1, A2, A3, . . . , An) that corresponds to identification number of each ultrasonic diagnostic apparatus 100; patient ID (PT1, PT2, PT3, . . . , PTn) that corresponds to identification number of each patient; examination date and time; B-mode use time; Doppler mode use time; color mode (CFM mode), M mode, ultrasonic image freeze count; still image recording count; and VTR recording count. The other items of the analysis result contains information such as each of the use times of ultrasonic diagnostic angiography mode, TDI mode, THI mode, and measurement mode or rate of recording count to freeze count, type of work flow used in the ultrasonic diagnostic apparatus.

Next, in FIG. 3 described previously, the server 300 converts the analysis result data into data of predetermined format such as E-mail attached file as required, and transmits the data to the computer terminal 200 at the hospital site via a communication line CL based on communication protocols such as TCP/IP (step St15).

In response to this, as shown in FIG. 3, when the computer terminal 200 receives the analysis result data transmitted from the center 300 at the center site through processing of the CPU (not shown) (step St16), such analysis result data is converted into display data such as display format list (listings), graph, or image that is predetermined so that the system user easily evaluates the use state of the ultrasonic diagnostic apparatus 100 as required (step St17).

Figure 6:
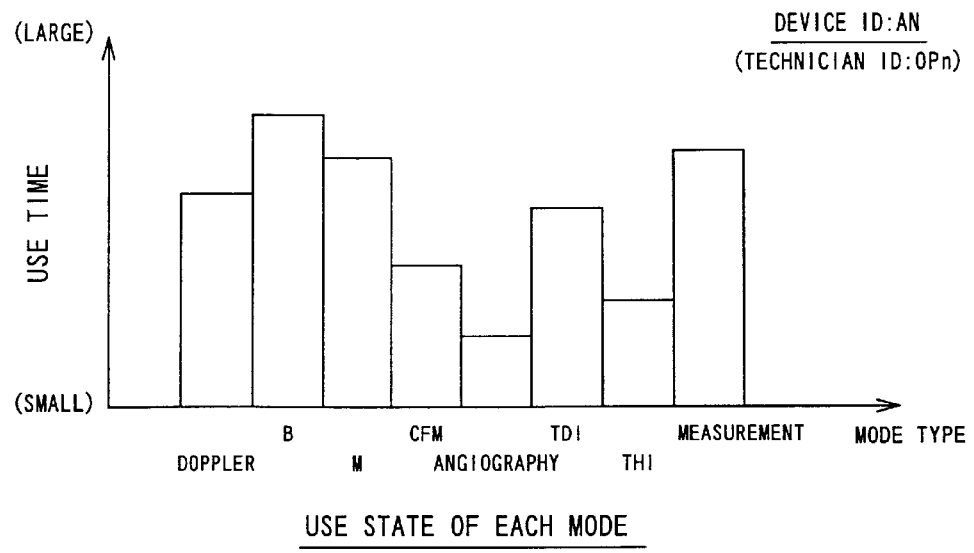
FIG. 6 is a graph illustrating a display example of the analysis result concerning the use state of each mode.
Figure 7:
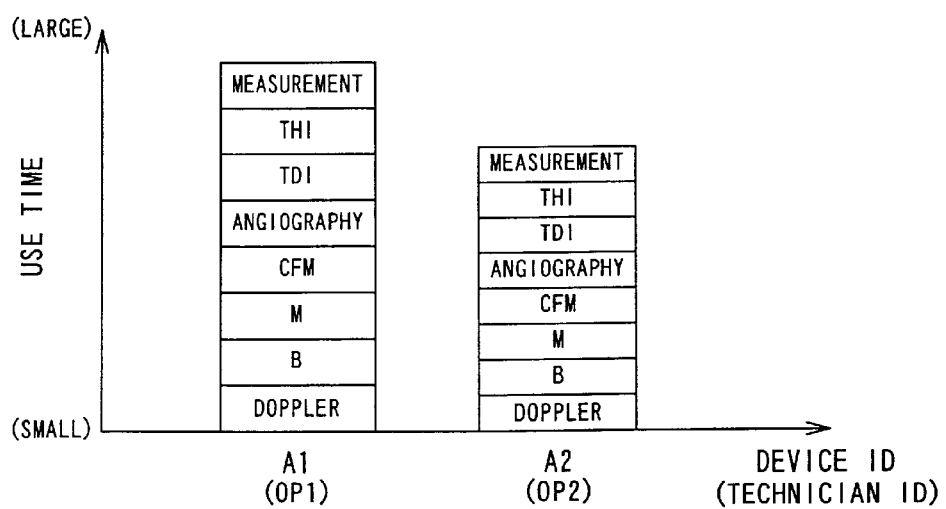
FIG. 7 is a graph illustrating a display example of the analysis result concerning the use state of each mode by apparatus or technician.
Figure 8:
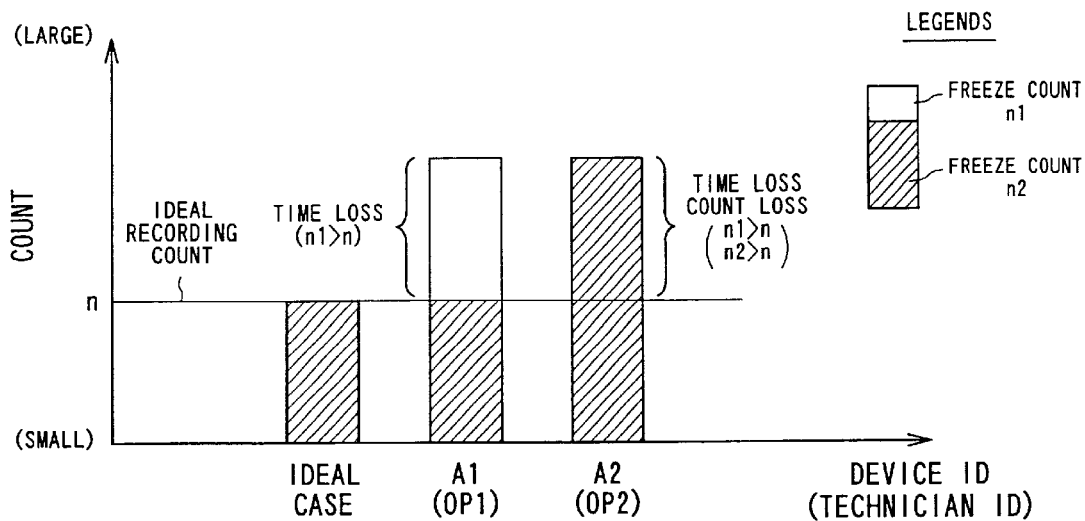
FIG. 8 is a graph illustrating a display example of the analysis result concerning recording efficiency of an ultrasonic image.

FIG. 6 to FIG. 8 illustrates an example of graphic representation of the analysis result data.

The graph of the analysis result data shown in FIG. 6 evaluates the use state of each mode (Doppler, B, M, CFM, angiography, TDI, THI, measurement or the like) within a predetermined period of time (such as within one month) by device ID or technician ID, where mode type is defined on a horizontal axis, and the use time of each mode is defined on a vertical axis, respectively. This example shows a case of ultrasonic diagnostic apparatus 100 whose device ID is An or a case of a technician whose technician ID is OPn. This makes it possible to easily evaluate the use state of the ultrasonic diagnostic apparatus 100 such as which mode is frequently or infrequently used.

The graph of the analysis result data shown in FIG. 7 evaluates the use time of each mode by device ID or technician ID, where device ID or technician ID is defined on a horizontal axis, and the use time of each mode is defined on a vertical axis, respectively. This example shows two cases in which the device ID is A1 and A2 (or technician D is OP1 and OP2), where a total value of the use time of each mode when the device ID is A2 (or technician ID is OP2) is greater than that of A1 (or technician ID is OP1). This result reflects a difference in use time of M mode, for example, in mode use times of these IDs.

From the foregoing, in view of an example of technician, a technician whose technician ID is OP1 takes relatively longer time required for examination than a technician whose technical ID is OP2 because time is required for B-mode examination. This makes it possible to relatively evaluate examination performance by technician.

The graph of the analysis result data shown in FIG. 8 evaluates the recording efficiency (successful recording rate) of an ultrasonic still image by each device ID (or technician) as compared with an ideal case, where device ID or technician ID is defined on a horizontal axis, and the freeze count "n1" and recording count "n2" of the ultrasonic image are defined on a vertical axis, respectively. In the present embodiment, the ideal case assumes that the freeze count "n1" and recording count n2 of the ultrasonic image each is equal to the ideal recording count "n" (freeze count: recording count=n1:n2=n:n).

In the present embodiment, as shown in FIG. 8, in the case where the device ID is A1 (or technician ID is OP1), although the recording count "n2" is equal to the ideal recording count "n", the freeze count "n1" is greater than the ideal recording count "n" (n1>n). From the foregoing, in view of an example of technician, in the case of a technician whose technician ID is OP1, although the still image recording count (number of records) is ideal, the freeze count is greater that the ideal case, thus enabling evaluation that a loss occurs with an examination time. In addition, as shown in FIG. 8, in the case where the device ID is A2 (or technician ID is OP2), the rate between the freeze count "n1" and recording count "n2" is 1, which is greater than the ideal recording count "n" in any case (n1>n and n2>n). From the foregoing, in view of an example of technician, in the case of a technician whose technician ID is OP2, although the successful recording rate is high based on the rate of recording count (number of records) of still image relevant to the freeze count, any of the freeze count and recording count is greater than the ideal case, thus enabling evaluation that an loss in examination time and a loss in the number of records occur.

Therefore, the present embodiment enables evaluation of the use state of the ultrasonic diagnostic apparatus as described above. Thus, maintenance such as periodic inspection or part replacement can be performed according to the use mode of each device ID, and a maintenance plan can be established. Further, the examination performance by technician can be evaluated in detail and easily by examination, and an improvement plan for improving examination efficiency by technician can be established. This is useful from an aspect of hospital management.

In addition, the thus obtained data concerning the use state of the ultrasonic diagnostic apparatus can be associated with data concerning patient's diseases additionally obtained (such as liver dysfunction, stone or pancreatitis) each other. In this case, the above described effect can be improved more significantly, for example, by comparing/evaluating the examination time of each mode by each patient's disease.

Although the above example describes a case in which a log data is used as data for analyzing/evaluating the use state of the ultrasonic diagnostic apparatus, it is possible to use ultrasonic probe degradation information; date and time information if the measurement value from an acceleration sensor exceeds a predetermined value; or its associated count information. In particular, use of information based on the measurement value from the acceleration sensor makes it possible to more precisely grasp the use state concerning movement of an ultrasonic probe which is hardly grasped from log data (degree of vibration or shock) and to efficiently implement maintenance such as inspection or repair.

Figure 9:
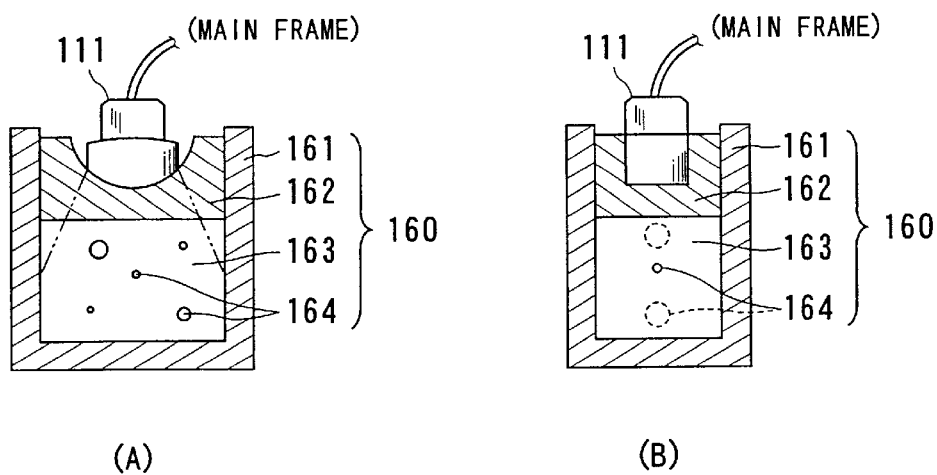
FIG. 9A and FIG. 9B are views each showing an outline of a probe holder used for phantom testing, where

In addition, as ultrasonic probe degradation information, it is possible to use known phantom test result as well as the above information. An example when this phantom test is used will be described with respect to FIG. 9 and FIG. 10.

FIG. 9A and FIG. 9B each illustrate an outline of a phantom test using an ultrasonic probe 111. In FIG. 9A and FIG. 9B, a phantom test is periodically implemented while the ultrasonic probe 111 is placed in the probe holder 160.

Figure 10:
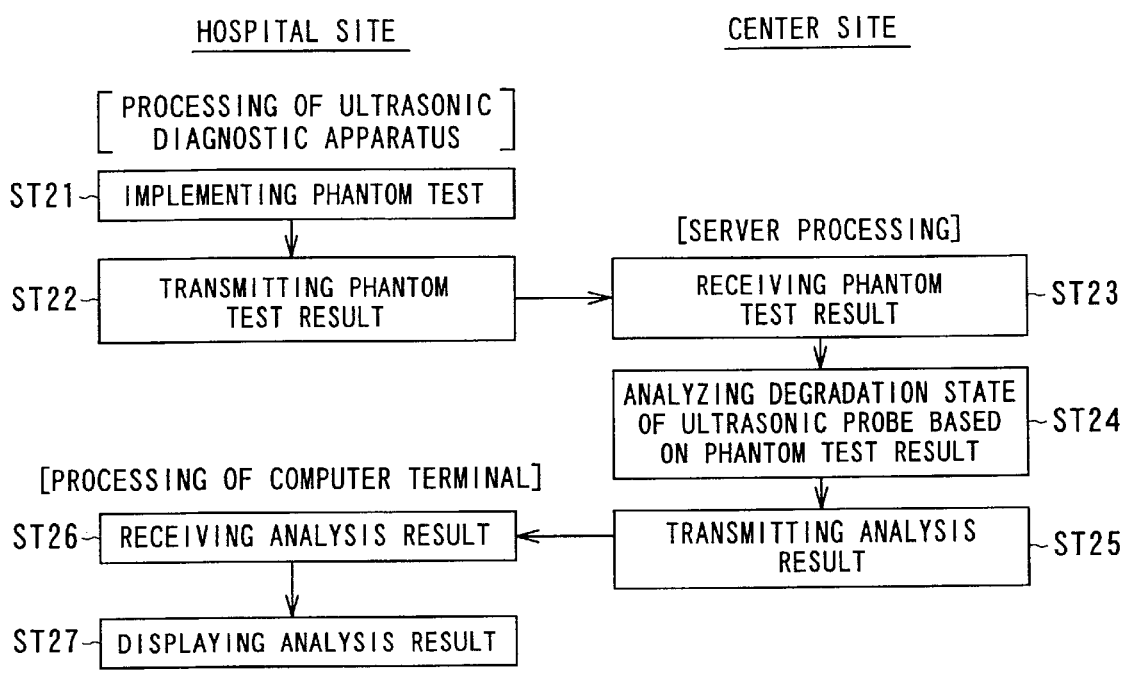
FIG. 10 is a chart illustrating a processing sequence between the ultrasonic diagnostic apparatus during phantom testing and maintenance system of the same.

The probe holder 160 shown in the present embodiment comprises: a holder case 161 that consists of its outer frame; a probe placement base (probe receiving member) 162 having a recess (groove) capable of engaging a probe tip end of the ultrasonic probe 111, the base being capable of inserting the ultrasonic probe 111 into the recess so as to be engaged therein and supported thereby; and a phantom 163 that consists of a standard phantom testing body placed at the base side of the probe placement base 162, as shown in FIG. 9A and FIG. 9B. Among them, at the phantom 163, as shown in FIG. 9A and FIG. 9B, there are disposed ultrasonic reflection bodies 164, . . . 164 made of a predetermined material (for example, tungsten) for phantom testing at plural positions inside of the phantom. FIG. 10 illustrates an outline of a processing sequence between the ultrasonic diagnostic apparatus 100 at the hospital site during phantom testing and the maintenance system MS at the center site.

In FIG. 10, the ultrasonic diagnostic apparatus 100 implements phantom testing under the control of the control portion 127 (step St21). This phantom testing is automatically started at a time when the system user makes preset button operations or the like or when the ultrasonic probe 111 is placed in the probe holder 160. In this manner, the ultrasonic probe 111 placed in the probe holder 160 is driven under predetermined ultrasonic scanning conditions. As a result, there is acquired an ultrasonic image that reflects the ultrasonic reflection bodies 164 . . . 164 in the phantom 163.

The ultrasonic diagnostic apparatus 100 transmits an ultrasonic image (phantom test result data) obtained by the phantom test to the maintenance system at the center site through a communication line CL (step St22).

In response to this, as shown in FIG. 10, when the maintenance system MS receives an ultrasonic image obtained by the phantom test, the ultrasonic image being transmitted from the ultrasonic diagnostic apparatus 100, through processing of the server 300 (step St23), the degradation state of the ultrasonic probe 111 is analyzed based on the ultrasonic image by using an image processing algorithm for known phantom testing, for example (step St24). The analysis result data is converted into data in accordance with a predetermined format such as E-mail attached file as required as in the case of the log data described previously, and then, is transmitted to the computer terminal 200 at the hospital site through a communication line CL based on communication protocols such as TCP/IP (step St25).

In response to this, as shown in FIG. 10, when the computer terminal 200 receives analysis result data transmitted from a server 300 at the center site through CPU processing (not shown) (step St26), the analysis result data is converted into display data in a predetermined display format so that the system user easily evaluates the degradation state of the ultrasonic probe 111 as required, and then, is displayed on the screen (step St27).

Apart from the above described phantom test, in order to evaluate the degradation information on the ultrasonic probe, it is possible to use a test caused by leaving a known ultrasonic probe in air. In this case, the ultrasonic probe is driven by each element while the probe is left in air, thereby enabling analysis for detection of a defective element or the like based on such reflection echo signal. Although the present embodiment describes an exemplary configuration of analyzing the use sate of the ultrasonic diagnostic apparatus or degradation state of the ultrasonic probe by a maintenance system placed at the remote center site, it is possible to mount a function for maintenance system data analysis or a database function integrally in the ultrasonic diagnostic apparatus. In this case, it becomes possible to analyze/evaluate the use state of the ultrasonic diagnostic apparatus or the degradation state of the ultrasonic probe, as described above.

Second Embodiment

Figure 11:
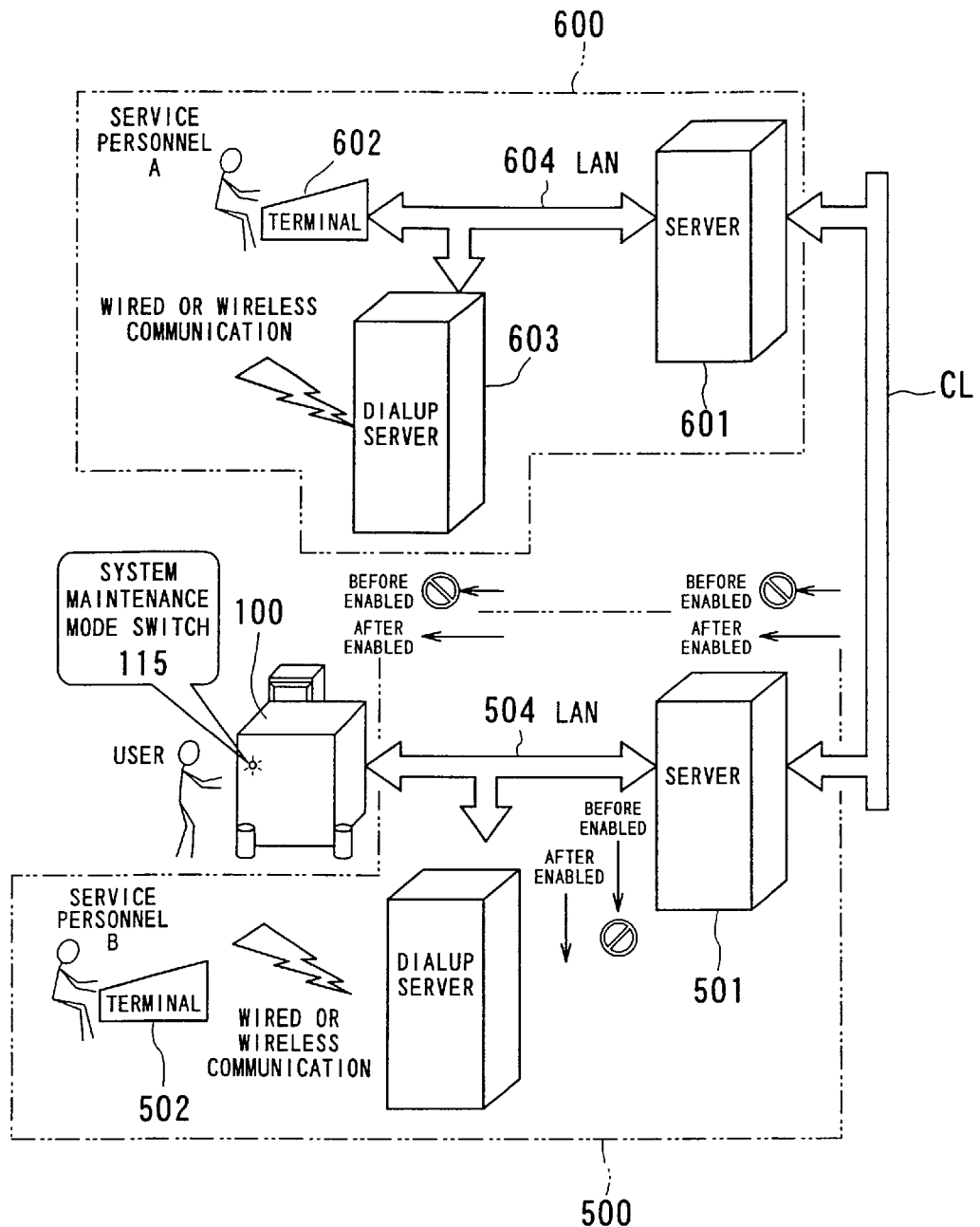
FIG. 11 is a schematic block diagram illustrating a medical imaging diagnostic apparatus and a maintenance method of the same according to a second embodiment of the present invention.

FIG. 11 illustrates an outline of a medical imaging diagnostic apparatus according to a second embodiment of the present invention (an ultrasonic diagnostic apparatus in the present embodiment) and a maintenance method of the same.

An ultrasonic diagnostic apparatus 100 that is a medical imaging diagnostic apparatus according to the second embodiment shown in FIG. 11 has a configuration similar to that shown in FIG. 2 described previously. This apparatus is connected to a computer network (hereinafter, referred to as a "local network") 500 constructed in hospital site or the like.

In the local network 500, according to the present embodiment, apart from a server 501 that functions as a nucleus for controlling network management, there are placed: a computer terminal (including radio terminal) 502 such as PC (personal computer) operated by service personnel or the like; and a dialup server (or modem 503. Together with these devices 501 to 503 each, the ultrasonic diagnostic apparatus 100 is connected communicably via a LAN 504.

Among them, the server 501 mounts a predetermined network OS (such as Windows NT or UNIX based OS and the like available from US. Microsoft Co., Ltd.). Under such OS environment, this server consists of a computer machine capable of executing an algorithm (an application program) that provides a variety of services according to a request from a network connection device (client) based on communication protocols such as TCP/IP. In the present embodiment, the server undergoes management/control for each domain that can be managed under the OS environment of Windows NT, for example (a server having this function is referred to as a "domain controller" in Windows NT).

This local network 500 is connected to enable communication with a computer network (hereinafter, referred to as a "service center internal network") constructed in a service center via a communication line CL such as leased line or public line.

In the service center internal network 600, according to the present embodiment, apart from a server 601 (corresponding to a server 300 at the center site described previously) that functions as a nucleus for controlling network management, there are placed a computer terminal 602 operated by service personnel or the like, and a dialup server 603 capable of making dialup IP connection by way of wired or wireless communication. These devices 601 to 603 each are connected communicably via a LAN 604.

With the above configuration of network connection, the ultrasonic diagnostic apparatus 100 according to the present embodiment enables a variety of data communications or reception of the associated services. For example, in he local network 500, it is possible to provide access to the dialup server 503 or making communication for remote service work with the service center internal network 600.

The ultrasonic diagnostic apparatus 100 executes an operation and function of the apparatus 100, for example, a service function or a patient information access function, which is different from general diagnosis, for the purpose of repair, fault diagnosis, or periodic inspection based on the user's instruction or the like from an operating panel. For example the apparatus makes communication concerning service processing with the service center internal network 600; sets or changes network connection environment of the ultrasonic diagnostic apparatus 100 or user profile and the like; or provides security management for the service function or access function and the like in response to startup of a system maintenance mode switch 115.

The ultrasonic diagnostic apparatus 100 displays a logon (login) screen prompting preset use ID or password entry on a predetermined screen of an operating panel (or monitor and the like), for example, when the power is turned ON; enables only a switch (an operating panel switch or a system mode switch 115) required for such input operation; and restricts operation of the other switches and functions according to the user. In this case, it is possible to restrict a privilege for operating the service function or patient information access function for a user that undergoes logon by way of an account of a default user or the like preset immediately after the power has been turned ON.

Now, exemplary processing concerning a security operation of a service function of the ultrasonic diagnostic apparatus 100 will be described with reference to FIG. 11.

In FIG. 11, an operator having a legal account capable of logging in the ultrasonic diagnostic apparatus 100 assumes a user who undergoes general examination using the ultrasonic diagnostic apparatus 100 and service personnel. In this case, the service personnel include: service personnel A who operates a terminal 602 of a service center internal network 600; and service personnel B who operates a terminal 503 of a local network 500. In addition, a server 501 of the local network 500 provides network management for connection devices such as ultrasonic diagnostic apparatus 100 or terminal 503 that participate in the domain in the local network 500.

First, during access to a service function, in order to prevent spoofing by an malicious third person, a security setting circuit performs user authentication to check whether or not an operator having its legal account (such as user who undergoes examination or service personnel A and B in the present embodiment) undergoes logon. Although this user authentication is based on password or the like in the present embodiment, it is possible to utilize information on user's body (fingerprint, iris patter, retina pattern, or facial profile or the like), for example, without being limited thereto.

As a result of the above user authentication, in the case where an operator having its legal account undergoes login, a privilege according to such operator is assigned. Hereinafter, an example of setting this privilege will be described.

First, startup of the system maintenance mode switch for starting up services on the operating panel is restricted to a user who undergoes general examination. For example, a privilege for providing services is not assigned.

Next, it is required for service personnel to enter a domain to which the ultrasonic diagnostic apparatus 100 of the local network 500 belongs in order to service work. However, service personnel are not assigned a privilege for entering such domain in an initial state.

In the present embodiment, there can be employed a method for actuating the system maintenance mode switch through the user at the ultrasonic diagnostic apparatus 100, thereby enabling access to the domain and ultrasonic diagnostic apparatus 100. The system maintenance mode switch 115 is actuated by button selection from the preset apparatus management menu, for example. As an example, this button selection is made when the system maintenance mode switch 115 of the ultrasonic diagnostic apparatus 100 is actuated by user operation after the user at the apparatus has asked service personnel A at the service center for investigation during periodic inspection, for example.

In this manner, the ultrasonic diagnostic apparatus 100 communicates with the server 501 that belongs to a domain of the local network 500 so as to enable access to such domain from the terminal 602 of service personnel A. Then, the apparatus performs control so as to enable logon to be provided to the ultrasonic diagnostic apparatus 100 of service personnel A. Here, an account of the service personnel A has a privilege for starting up a service function, for example.

Therefore, after the ultrasonic diagnostic apparatus 100 has logged on, there is performed a service function from the terminal 602 of service personnel A, for example, an operation for starting up a self diagnosis test to check an operation of the apparatus itself required for periodic inspection. The test result is read in a recording medium incorporated in the ultrasonic diagnostic apparatus 100 (for example, a recording medium such as memory or disk of the security setting circuit 129 in FIG. 2 described previously), and is transferred to the service center through a network via an interface circuit (refer to FIG. 2 described previously), whereby abnormality check of the ultrasonic diagnostic apparatus or its related recording is performed. In addition, an image of a test pattern when produced from the input of each block of the ultrasonic diagnostic apparatus 100 is also transferred similarly from the apparatus 1 to the service center via a network. Further, a daily error log or an event log is read out from a recording medium (for example, a recording medium such as memory or disk in the security setting circuit) in the ultrasonic diagnostic apparatus similarly, and is transferred to the service center via a network.

In addition, all privileges concerning service can be assigned to service personnel A. However, in this case, there is not assigned a privilege for performing reading or writing for patient image data, electronic medical chart, and examination reservation system (not shown) that are present in a network 100 to which the ultrasonic diagnostic apparatus 100 belongs, thereby making it possible to prevent the infringement of privacy.

Further, in the case where service personnel A is required to access these items of information in order to check an operation of the ultrasonic diagnostic apparatus or refer to an abnormal record, a user having its privilege to enable such access is asked to start up the system maintenance mode switch 115 (access privilege enable switch) for patient data set to the ultrasonic apparatus 100, thereby making it possible to validate his or her own access privilege. This privilege is eliminated by service personnel A issuing a service completion report, i.e., by service personnel A recording service completion in an even log of the apparatus 1 or a user pressing a switch for reverting a patient data access privilege to its initial state.

In addition, an access privilege can be set relevant to service personnel by limiting time. For example, in the case where the day of the week for periodic inspection with service work is set to Saturday, it is possible to release such privilege in advance so as to permit a privilege assigned to service personnel A on Friday to be transferred to only the morning of Saturday. This applies to a case in which one inspection a month is performed. In this case as well, a privileged user may release a privilege for inspection. In the case where the user cannot make an operation concerning such release of privilege, the service center delivers to the user the associated setting program or script and the like, and merely opens and executes the program or script, thereby enabling presetting.

Access privileges having plural privilege levels can be set relevant to service personnel A. For example, these privileges are divided into a privilege concerning maintenance and a privilege for incorporated software version upgrade or system region information rewriting, and the privileges are assigned according to the ability or qualification of service personnel. This is because a serious problem may occur with an operation of the apparatus 1 if service personnel performs incorporated software version upgrade of an advanced control system or system region information rewriting without sufficient knowledge.

In addition, some network environments to which the ultrasonic diagnostic apparatus 100 belongs may require advanced security management for service personnel. In order to cope with this necessity, it is possible to employ a rule in which a password is changed in an encoded manner with an elapse of time. This rule is intended to avoid a circumstance in which a fixed password is communicated in a network, and privacy cannot be protected sufficiently.

In this case, procedures for establishing the rule for changing a password with an elapse of time is preset in a recording medium incorporated in a security setting circuit (refer to FIG. 2 described previously), for example, in the ultrasonic diagnostic apparatus 100. A mechanism for changing a password that service personnel use is similar to password issuance caused by a security card, for example. By performing the procedures, even if an account name or password over a network is hacked by a third person, these count name and password are changed one after another, thus making it possible to more effectively prevent spoofing by the third person.

In addition, the security setting circuit (refer to FIG. 2 described previously), for example, in the ultrasonic diagnostic apparatus 100 can have a function for detecting and restricting the fact that an access is provided by an incorrect password or unregistered account. With this function, in the case where an illegal access reaches a predetermined count, the logon of such account is disabled, and the logon provided to the ultrasonic diagnostic apparatus 100 is disabled in all the accounts other than a specific account of a supervisor or the like. At the same time, an occurrence of an illegal access is notified to service personnel or service center. In this manner, external malicious logon is prevented.

On the other hand, even in the case where legal logon is performed, in order to prevent service personnel from failing to logoff, for example, when the service personnel leave a desk during logon for a long time, and illegal use in such state, if a service or examination function or remote or direct panel operation is not performed for a predetermined time (for example, 20 minutes) after logon having a service privilege has been done, an inoperable state is established unless personal authentication identical to that during logon is performed. In this state, shutdown or restart is possible, but operation cannot be continued.

As means for checking that an access from the service center is provided, apart from the above method, it is possible to restrict a terminal IP address, to employ electrical authentication, or to restrict telephone line number or the like.

Service logon can be directly performed from an operating panel of the ultrasonic diagnostic apparatus 100 as well as via network as described above. In this case, in general, the ultrasonic diagnostic apparatus 100 does not have an individual authentication function such as fingerprint. Thus, it is desirable that all the privileges available for use in service with only passwords (in particular, fixed passwords) be disabled. Even in the case where one is situated near the ultrasonic apparatus 100, it is possible to provide logon to the apparatus 1 from the local network 100 by utilizing a hand held terminal.

In addition, if an abnormality in the ultrasonic diagnostic apparatus 100 has been found when the power is supplied, an instruction is assigned to an operator on the screen or E-mail is sent to a user. Further, connection to the service center site is made via a network, and a password is automatically transmitted in the case where the contents and data is reported. During this report, as described above, it is desired that a password changing with an elapse of time be used or electronic authentication be used.

As a result of automatic response of this report, in the case where there occurs an abnormality requiring an instruction for first aid from the service center site, the setting is provided to automatically enable logon from the service center site. The privilege of this emergency logon account is restricted to this function (first aid) to be discriminated from general service account, thereby preventing security from being lowered. For example, it is unreasonable that a user has logon permission. Thus, it is desirable that automatic connection from the service center site can be made.

In the present embodiment, although a description has been given by way of example concerning the service function, security can be ensured in a similar way when logon is provided to a domain or device for the purpose of remote diagnosis.

Figure 12:
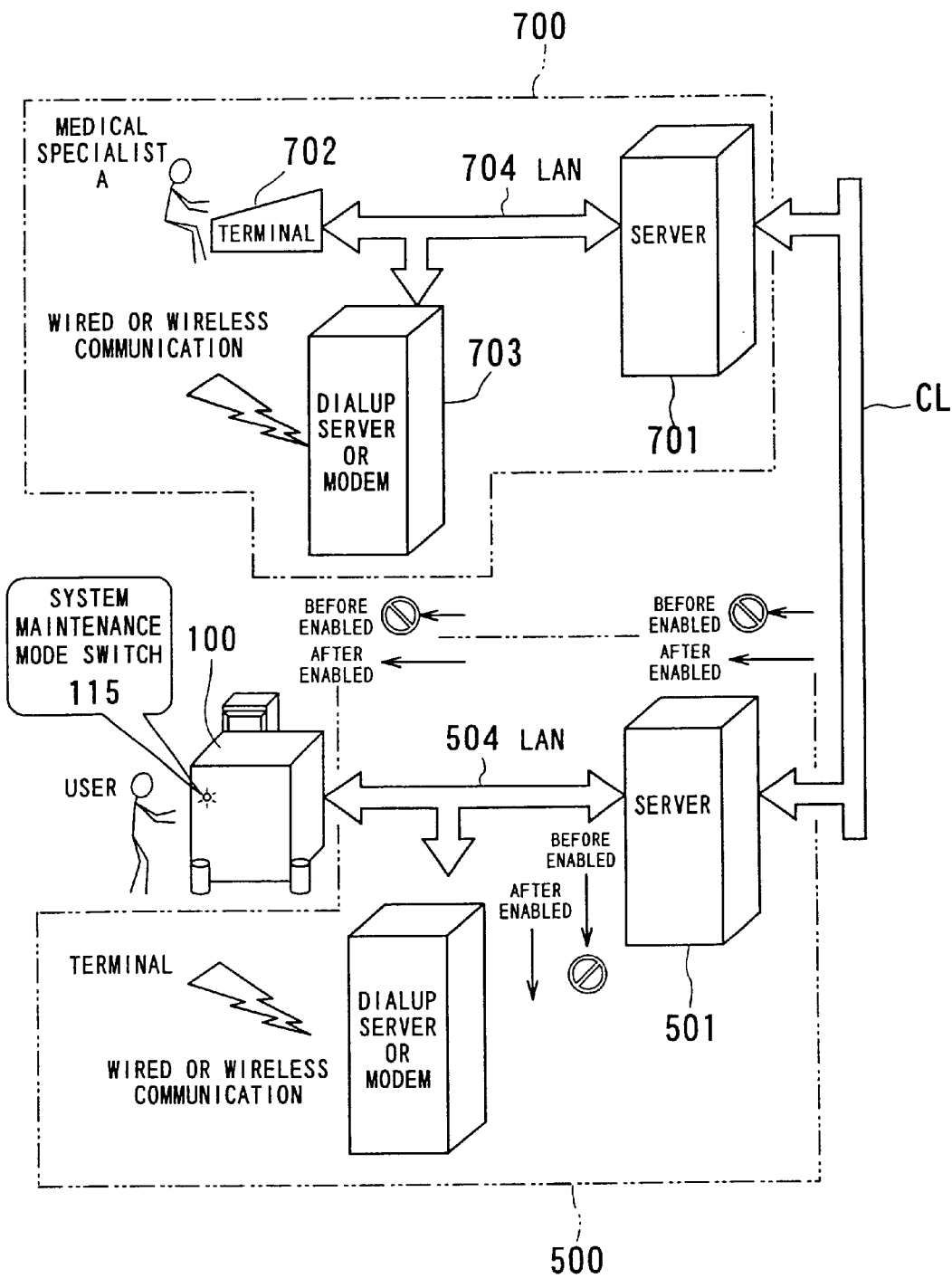
FIG. 12 is a view illustrating an example applied in the case of remote diagnosis in the second embodiment of the present invention.

For example, as shown in FIG. 12, assume that a user (examination technician) who is an operator of the ultrasonic diagnostic apparatus 100 asks remote medical specialist A to diagnose a specific disease.

In this case, a network (hereinafter, referred to as a remote network) 700 is constructed at a site of the hospital to which medical specialist A belongs, as is the case with the service center. In this remote network 700, a device such as a server 701 (corresponding to a server 300 at the center site described previously), a terminal 702 operated by medical specialist A or the like, a dialup server 703 is connected communicably via a LAN 704. This remote network 700 is connected to a local network 500 via a communication line CL such as leased line or public line.

First, a remote diagnosis startup switch playing a role similar to the system maintenance mode switch 115 in the ultrasonic diagnostic apparatus 100 is started up for an account of the remote medical specialist A, and this medical specialist is selected as a connection partner.

Through this processing, medical specialist A enters a domain to which the ultrasonic diagnostic apparatus 100 belongs, and logon is provided to this ultrasonic diagnostic apparatus 100. After logon, the medical specialist diagnoses a patient through the screen of his or her own terminal 702 or by changing the settings of the ultrasonic diagnostic apparatus 100 from his or her own terminal 702. The medical specialist can undergo diagnosis by acquiring patient information such as past patient data or another diagnostic apparatus data or electronic medical chart is acquired from a patient database or server 501 over a network to which the ultrasonic diagnostic apparatus 100 belongs, while referring to these items of information.

At this time, whether or not to release access privileges of all the patient information is set in advance or when remote diagnosis is enabled. When remote diagnosis terminates, processing for therapeutic activities of medical specialist A is performed for a medical therapeutics reward system as required, and patient data is transferred to a server or the like. When remote diagnosis is terminated, an access privilege of this medical specialist A relevant to domain, device and patient data is eliminated. In order to continuously undergo remote diagnosis, a question of whether nor not to continue an access privilege is issued to enable continuous use.

Therefore, according to the present embodiment, there is provided a function for restricting privileges for remote diagnosis of the ultrasonic diagnostic apparatus, patient data management, or remote service function by individuals or organizations, and identifying registered individuals or organizations relevant to an operator or a remote connecting entities. In this manner, there can be provided a highly satisfied medical activities for a patient by easily providing these settings of restriction without special knowledge, safely utilizing convenience caused by network capabilities or the like, and reducing medical cost.

Third Embodiment

Figure 13:
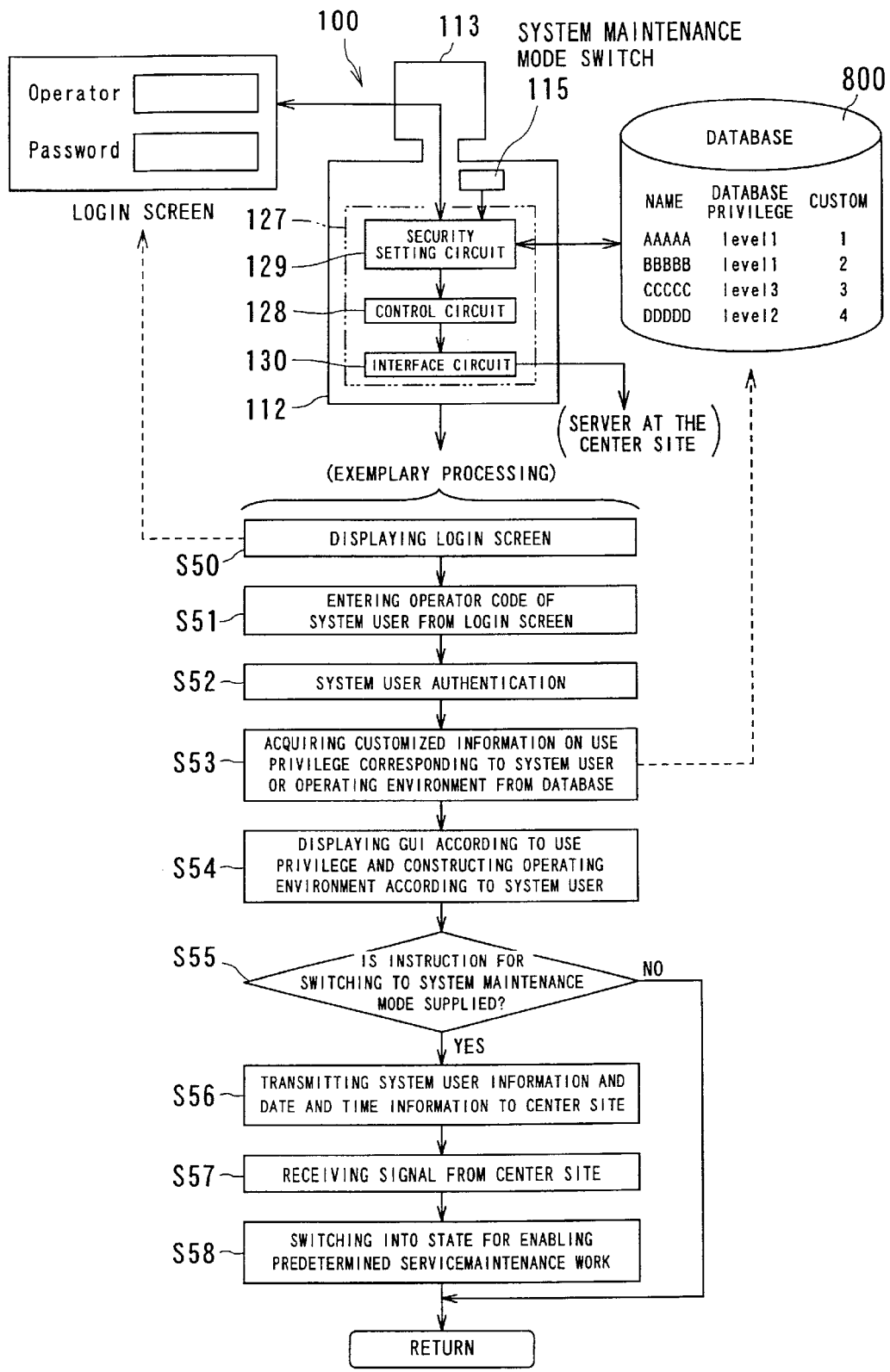
FIG. 13 is a schematic block diagram illustrating a medical imaging diagnostic apparatus and a maintenance method of the same according to a third embodiment of the present invention.

FIG. 13 illustrates a medical imaging diagnostic apparatus according to a third embodiment of the present invention (an ultrasonic diagnostic apparatus in the present embodiment) and a maintenance method of the same. In an ultrasonic diagnostic apparatus 100 shown in FIG. 13, apart from a configuration similar to the above (In FIG. 13, a monitor 113, a main frame 112, a control portion 112, and a control portion 127 (a control circuit 128, a security monitor 113, and an interface circuit 130) in FIG. 2 described above and only a system maintenance mode switch 115 are illustrated on a storage medium (not shown) in the ultrasonic diagnostic apparatus 100. This database 800 can be constructed on a storage medium in a computer over a network (for example, a local network 500) via which the ultrasonic diagnostic apparatus 100 is connected communicably.

In the database 800, information on "use privilege" and "customized information" on the operator specific operating environment are data-registered as its attribute for each system user (each user) so that the information can be managed.

Among them, with respect to the information on "use privilege", two or more levels, for example, an operator level, an administrator level, and a service personnel level are set according to the user, for example. In the present embodiment, there are exemplified three levels 1 to 3, i.e., level 1 (a doctor or examination technician undergoing operation concerning general examination); level 2 (network administrator undergoing setting and change of an IP address or the like in network environment to which the ultrasonic diagnostic apparatus 100 belongs); and level 3 (service personnel undergoing fault diagnosis or the like of the ultrasonic diagnostic apparatus 100) in order of the lowest use privilege.

In addition, the "customized information" contains information concerning operating environment for a user interface such as GUI, initial value information, system presetting and the like. In the present embodiment, customs (reference indexes) 1 to 4 are set by each user.

Now, exemplary processing according to the present embodiment will be described with reference to FIG. 13.

First, at the step S50, during device login, a screen (a login screen) prompting entry of at least one of an operator code and its password is displayed on a monitor 113 that is a user interface.

Then, at the step S51, when the operator code or the like is entered by the system user, user authentication is performed at the step S52 based on such input. In this user authentication, if it is judged that a user is not registered, the subsequent operation cannot be performed or a default user is logged in at the lowest level of a use privilege.

In the case where it is judged at the above step S52 that a user has been registered, the user is searched for and correlated by using a database 800 at the step S53. Then, there are obtained customized information concerning the operator specific operating environment, the information being registered in the database 800, and information on use privileges relevant to a variety of functions. At the step S54, the GUI display according to these items of the customized information and information on use privileges is performed on the monitor 113, whereby the operating environment according to the operator is constructed. Hereinafter, for example, only an input switch related to a privileged function is displayed. Alternatively, only a hard switch assigned to such function can be used.

In the case of a conventional ultrasonic diagnostic apparatus, it is known that operating environment preferred by a user or functions for service personnel are provided or preserved for each operator. Any of these functions are such that an operator selects operating environment from one menu or the like or enter a password. In this case, there is a possibility that even a human being other than an operator use or can use these functions. Therefore, there has been a problem with device security.

In contrast, according to the present embodiment, in particular, with respect to a case in which preferred operating environment is provided to each operator or a function concerning security or the like of the ultrasonic diagnostic apparatus 100, for example, a restriction applies to functions available for use according to service personnel, administrator or general operator. In this way, a user name and a password is requested during startup of the ultrasonic diagnostic apparatus 100, during logon, or during operator change so that only privileged functions can be used from a use privilege assigned to a user registered in advance in the apparatus. Thus, the function use privileges according to the user levels are divided, and the security of the ultrasonic diagnostic apparatus 100 can be ensured more reliably as compared with a conventional example.

An operator such as an administrator can generate a use privilege as required. In this case, there can be employed a technique of generating a new privilege level and assigning the use privilege of a function corresponding to such privilege level. In addition, a new privilege level can be assigned during operator registration.

Next, in maintenance of the ultrasonic diagnostic apparatus 100, as shown in FIG. 13 described above, it is judged whether or not an instruction for switching into a system maintenance mode is assigned by the system user operating the system maintenance mode switch 115 (step S55). Only in the case where it is judged as YES (an instruction for switching into a system maintenance mode is assigned), information concerning the system user and the date and time information are transmitted to a server 501 or a server 601 at the center site (step S56). In response to this, a state for enabling at least one of system diagnosis of the ultrasonic diagnostic apparatus 100, system setting change, and control program change is established based on a control signal for predetermined approval for maintenance transmitted from the server 501 or server 601 at the center site (steps S57 and S58). In this manner, a predetermined maintenance work is implemented by the system user. In addition, it is possible to keep records concerning the system user's approval for maintenance.

In each of the above embodiments, although an ultrasonic diagnostic apparatus is exemplified as a medical imaging diagnostic apparatus, the present invention is applicable to various medical imaging modalities such as an X-ray diagnostic apparatus, a CT scanner, an MRI, a nuclear medical diagnostic apparatus, and an endoscope without being limited thereto.

According to the present invention, various modifications can occur without departing the spirit of the invention without being limited thereto.

Additional advantages and modifications will readily occur to those skilled in the art. Therefore, the invention in its broader aspect is not limited to the specific details and representative embodiments shown and described herein. Accordingly, various modifications may be made without departing from the spirit or scope of the general inventive concept as defined by the appended claims and their equivalents.

What is claimed is:

1. A method of a medical imaging diagnostic apparatus by a remote computer connected via a communication line, the method comprising the steps of:

generating log data pertaining to a use state of the medical imaging diagnostic apparatus;

transmitting the generated log data to the remote computer via the communication line;

storing the transmitted log data as data in a predetermined database on the remote computer; and analyzing the use state of the medical imaging diagnostic apparatus so that the use state can be quantitatively displayed based on the log data stored in the database, wherein the medical imaging diagnostic apparatus is an ultrasonic diagnostic apparatus, and wherein the analysis result of the use state of the medical imaging diagnostic apparatus includes at least one of (i) the number of patients diagnosed within a predetermined period of time by the ultrasonic diagnostic apparatus, (ii) each use time of an ultrasonic diagnostic Doppler mode, a B mode, M mode, a CFM (Color Flow Mapping) mode, an angiographic mode, a TDI (Tissue Doppler Imaging) mode, a THI (Tissue Harmonic Imaging) mode, and a measurement mode used by the ultrasonic diagnostic apparatus, (iii) a freeze count of an ultrasonic image displayed by the ultrasonic diagnostic apparatus, (iv) an ultrasonic image recording count, and (v) a rate of the recording count to the freeze count.

2. The method of a medical imaging ultrasonic diagnostic apparatus according to claim 1,
wherein the analyzing step analyzes the use state of the medical imaging diagnostic apparatus so that the use state can be graphically displayed based on log data stored in the database.

3. A method of a medical imaging ultrasonic diagnostic apparatus by a remote computer connected via a communication line, the method comprising the steps of:
generating log data pertaining to a use state of the medical imaging diagnostic apparatus;
transmitting the generated log data to the remote computer via the communication line;
storing the transmitted log data as data in a predetermined database on the remote computer; and
analyzing the use state of the medical imaging diagnostic apparatus so that the use state can be displayed based on log data stored in the database,
wherein the medical imaging diagnostic apparatus is an ultrasonic diagnostic apparatus having an ultrasonic probe, and the data includes at least one of:
degradation information on the ultrasonic probe;
information on date and time when a measurement value obtained by an acceleration sensor provided at the ultrasonic probe exceeds a predetermined value; and
information on the count when the measurement value obtained by the acceleration sensor exceeds a predetermined value.

4. The method of a medical imaging ultrasonic diagnostic apparatus according to claim 3,
wherein the analyzing step analyzes the use state of the medical imaging diagnostic apparatus so that the use state can be graphically displayed based on log data stored in the database.

5. A method of a medical imaging diagnostic apparatus, comprising the steps of:
generating log data pertaining to a use state of a medical imaging diagnostic apparatus;
recording the generated log data on a predetermined recording medium; and
analyzing the use state of the medical imaging diagnostic apparatus so that the use state can be quantitatively displayed based on the log data of the recording medium,
wherein the medical imaging diagnostic apparatus is an ultrasonic diagnostic apparatus, and
wherein the analysis result of the use state of the medical imaging diagnostic apparatus includes at least one of (i) the number of patients diagnosed within a predetermined period of time by the ultrasonic diagnostic apparatus, (ii) each use time of an ultrasonic diagnostic Doppler mode, a B mode, M mode, a CFM (Color Flow Mapping) mode, an angiographic mode, a TDI (Tissue Doppler Imaging) mode, a THI (Tissue Harmonic Imaging) mode, and a measurement mode used by the ultrasonic diagnostic apparatus, (iii) a freeze count of an ultrasonic image displayed by the ultrasonic diagnostic apparatus, (iv) an ultrasonic image recording count, and (v) a rate of the recording count to the freeze count.

6. The method of a medical imaging diagnostic apparatus according to claim 5,
wherein the analyzing step analyzes the use state of the medical imaging diagnostic apparatus so that the use state can be graphically displayed based on log data of the recording medium.

7. A medical imaging diagnostic apparatus comprising:
log generating means for generating log data pertaining to a use state of a medical imaging diagnostic apparatus;
log recording means for recording the log data generated by the log generating means on a predetermined recording medium; and
analysis means for analyzing a use state of the medical imaging diagnostic apparatus so that the use state can be quantitatively displayed based on the log data recorded on the recording medium by the log recording means,
wherein the medical imaging diagnostic apparatus is an ultrasonic diagnostic apparatus, and
wherein the analysis result of the use state of the medical imaging diagnostic apparatus includes at least one of (i) the number of patients diagnosed within a predetermined period of time by the ultrasonic diagnostic apparatus, (ii) each use time of an ultrasonic diagnostic Doppler mode, a B mode, M mode, a CFM (Color Flow Mapping) mode, an angiographic mode, a TDI (Tissue Doppler Imaging) mode, a THI (Tissue Harmonic Imaging) mode, and a measurement mode used by the ultrasonic diagnostic apparatus, (iii) a freeze count of an ultrasonic image displayed by the ultrasonic diagnostic apparatus, (iv) an ultrasonic image recording count, and (v) a rate of the recording count to the freeze count.

8. The medical imaging diagnostic apparatus according to claim 7,
wherein the analysis means analyzes a use state of the medical imaging diagnostic apparatus so that the use state can be graphically displayed based on log data recorded to the recording medium by the log recording means.

9. A medical imaging diagnostic apparatus configured to perform maintenance by means of a remote computer connected via a communication line, the apparatus comprising:
input means operably linked to the medical imaging diagnostic apparatus, and adapted to input information pertaining to a system user;
operating means operably linked to the medical imaging diagnostic apparatus, the operating means being adapted to instruct a change to a predetermined system maintenance mode;
transmission means for, when the change to the system maintenance mode is instructed by the operating means, transmitting to the remote computer the information concerning the system user inputted by the input means, including date and time information; and means for switching a current state into a state for enabling at least one of system diagnosis of the medical imaging diagnostic apparatus, system setting change, and control program change based on a signal transmitted from the remote computer via the communication line in response to the information transmitted by the transmission means.

10. A maintenance method of a medical imaging diagnostic apparatus by means of a remote computer connected via a communication line, the maintenance method comprising the steps of:
inputting information pertaining to a system user to the medical imaging diagnostic apparatus;
operating the medical imaging diagnostic apparatus, thereby instructing switching into a system maintenance mode for enabling at least one of system diagnosis of the medical imaging diagnostic apparatus, system setting change, and control program change based on a signal transmitted from the remote computer via the communication line in response to the inputted information;
transmitting information pertaining to the system user and including date and time information to the remote computer via the communication line when the switching into the system maintenance mode is instructed; and
storing the transmitted information concerning the system user and the date and time information to a predetermined recording medium on the remote computer.

11. A method of a medical imaging diagnostic apparatus by a remote computer connected via a communication line, the method comprising the steps of:
generating log data pertaining to a use state of the medical imaging diagnostic apparatus;
transmitting the generated log data to the remote computer via the communication line;
storing the transmitted log data as data in a predetermined database of the remote computer; and
analyzing the use state of the medical imaging diagnostic apparatus so that the use state can be quantitatively displayed based on the log data stored in the database,
wherein the medical imaging diagnostic apparatus is directed to an ultrasonic diagnostic apparatus, and the analysis result of the use state of the medical imaging diagnostic apparatus includes at least one of: a freeze count of an ultrasonic image displayed by the ultrasonic diagnostic apparatus; an ultrasonic image recording count; and a rate of the recording count to the freeze count.

12. A method of a medical imaging diagnostic apparatus by a remote computer connected via a communication line, the method comprising the steps of:
generating log data pertaining to a use state of the medical imaging diagnostic apparatus;
transmitting the generated log data to the remote computer via the communication line;
storing the transmitted log data as data in a predetermined database on the remote computer; and
analyzing the use state of the medical imaging diagnostic apparatus so that the use state can be quantitatively displayed based on the log data stored in the database,
wherein the medical imaging diagnostic apparatus is an ultrasonic diagnostic apparatus including an ultrasonic probe, and
wherein the ultrasonic diagnostic apparatus comprises:
a probe holder for holding the ultrasonic probe;
a phantom including a standard test body for phantom testing equipped in the probe holder;
means for obtaining an ultrasonic image of the phantom by the ultrasonic probe held in the probe holder; and
means for transmitting the ultrasonic image of the phantom as data for obtaining degradation information on the ultrasonic probe to the remote computer.

13. The method of a medical imaging ultrasonic diagnostic apparatus according to claim 12,
wherein the analyzing step analyzes the use state of the medical imaging diagnostic apparatus so that the use state can be graphically displayed based on log data stored in the database.

14. A method of a medical imaging diagnostic apparatus, comprising the steps of:
generating log data pertaining to a use state of a medical imaging diagnostic apparatus;
recording the generated log data on a predetermined recording medium; and
analyzing the use state of the medical imaging diagnostic apparatus so that the use state can be quantitatively displayed based on the log data of the recording medium,
wherein the medical imaging diagnostic apparatus is an ultrasonic diagnostic apparatus having an ultrasonic probe, and the data includes at least one of:
degradation information on the ultrasonic probe;
information on date and time when a measurement value obtained by an acceleration sensor provided at the ultrasonic probe exceeds a predetermined value; and
information on the count when the measurement value obtained by the acceleration sensor exceeds a predetermined value.

15. The method of a medical imaging diagnostic apparatus according to claim 14,
wherein the analyzing step analyzes the use state of the medical imaging diagnostic apparatus so that the use state can be graphically displayed based on log data of the recording medium.

16. A medical imaging diagnostic apparatus comprising:
log generating means for generating log data pertaining to a use state of a medical imaging diagnostic apparatus;
log recording means for recording the log data generated by the log generating means on a predetermined recording medium; and
analysis means for analyzing a use state of the medical imaging diagnostic apparatus so that the use state can be quantitatively displayed based on the log data recorded on the recording medium by the log recording means,
wherein the medical imaging diagnostic apparatus is an ultrasonic diagnostic apparatus having an ultrasonic probe, and the data includes at least one of:
degradation information on the ultrasonic probe;
information on date and time when a measurement value obtained by an acceleration sensor provided at the ultrasonic probe exceeds a predetermined value; and
information on the count when the measurement value obtained by the acceleration sensor exceeds a predetermined value.

17. The medical imaging diagnostic apparatus according to claim 16,
wherein the analysis means analyzes a use state of the medical imaging diagnostic apparatus so that the use state can be graphically displayed based on log data recorded to the recording medium by the log recording means.

* * * * *

UNITED STATES PATENT AND TRADEMARK OFFICE
CERTIFICATE OF CORRECTION

PATENT NO. : 6,656,119 B2
DATED : December 2, 2003
INVENTOR(S) : Sasaki et al.

Page 1 of 1

It is certified that error appears in the above-identified patent and that said Letters Patent is hereby corrected as shown below:

<u>Title page,</u>
Item [30], Foreign Application Priority Data, should read:

-- [30] Foreign Application Priority Data

Mar. 17, 2000 (JP) ……………………….. 2000-076808
Mar. 28, 2000 (JP) ……………………….. 2000-089707 --

Signed and Sealed this

Second Day of March, 2004

JON W. DUDAS
*Acting Director of the United States Patent and Trademark Office*